United States Patent [19]

Dybbs

[11] Patent Number: 5,674,233
[45] Date of Patent: Oct. 7, 1997

[54] OPHTHALMIC SURGICAL INSTRUMENT AND METHOD

[76] Inventor: Alexander Dybbs, 2588 Edgerton Rd., Cleveland, Ohio 44118

[21] Appl. No.: 433,333

[22] PCT Filed: Nov. 8, 1993

[86] PCT No.: PCT/US93/10797

§ 371 Date: Nov. 15, 1995

§ 102(e) Date: Nov. 15, 1995

[87] PCT Pub. No.: WO94/10918

PCT Pub. Date: May 26, 1994

Related U.S. Application Data

[63] Continuation-in-part of Ser. No. 972,756, Nov. 6, 1992, Pat. No. 5,308,355.

[51] Int. Cl.$^6$ .................................................. A61B 17/32
[52] U.S. Cl. ........................ 606/166; 606/170; 128/898
[58] Field of Search .................... 606/4, 5, 6, 107, 606/166, 167, 170, 172; 128/662.03, 662.05, 898

[56] References Cited

U.S. PATENT DOCUMENTS

| | | | |
|---|---|---|---|
| 4,499,898 | 2/1985 | Knepshield et al. | 606/166 |
| 4,526,171 | 7/1985 | Schachar . | |
| 4,546,773 | 10/1985 | Kremer et al. . | |
| 4,637,393 | 1/1987 | Ray | 606/166 |
| 4,665,914 | 5/1987 | Tanne . | |
| 4,674,503 | 6/1987 | Peyman et al. . | |
| 4,705,037 | 11/1987 | Peyman et al. | 606/166 |
| 4,742,829 | 5/1988 | Law et al. . | |
| 4,817,432 | 4/1989 | Wallace et al. . | |
| 5,090,955 | 2/1992 | Simon | 606/107 |
| 5,165,415 | 11/1992 | Wallace et al. . | |
| 5,222,967 | 6/1993 | Casebeer et al. | 606/166 |
| 5,308,355 | 5/1994 | Dybbs | 606/166 |
| 5,674,503 | 6/1997 | Peyman et al. | 606/166 |

OTHER PUBLICATIONS

Storz Ophthalmics Inc., "Refractive Keratoplasty" Catalogue (1992).
Chiron Ophthalmics, Brochure Entitled "Keratorefractive Surgery" (1991).
Kimi Surgical Products, Brochure Entitled "Radial and Astigmatic KeratotomyInstruments" (1992).
Radial Keratotomy, LAL Publishing, Chapter 23, pp. 201–211 (1980).
Sonogage News, Sonogage, Inc.
Sonogage News, "Radial Keratotomy", Sonogage, Inc.
Information Sheet, "The Sonogage Pachometry Technique", Sonogage, Inc.
Information Sheet, "Corneo–Gage", Sonogage Corneo–Gage.

Primary Examiner—Lee S. Cohen
Assistant Examiner—Michael Peffley
Attorney, Agent, or Firm—Renner, Otto, Boisselle & Sklar

[57] ABSTRACT

A corneal surgical instrument comprising a surgical knife and ultrasonic probe assembly (12) that measures the corneal thickness, monitors the positioning and perpendicularity of the knife (37) and controls the depth of the knife blade (37). The ultrasonic probe assembly (15) includes a pair of ultrasonic probes (47) disposed on opposite sides of the knife blade (37). Information on monitored parameters is displayed to the surgeon.

14 Claims, 5 Drawing Sheets

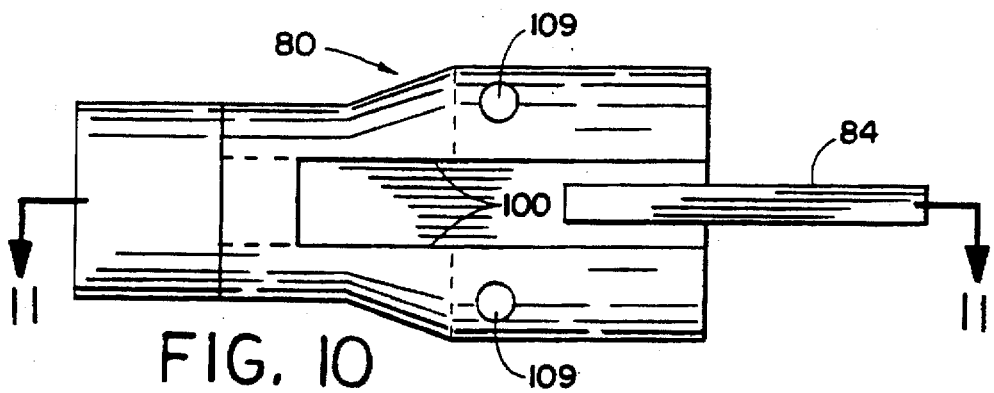
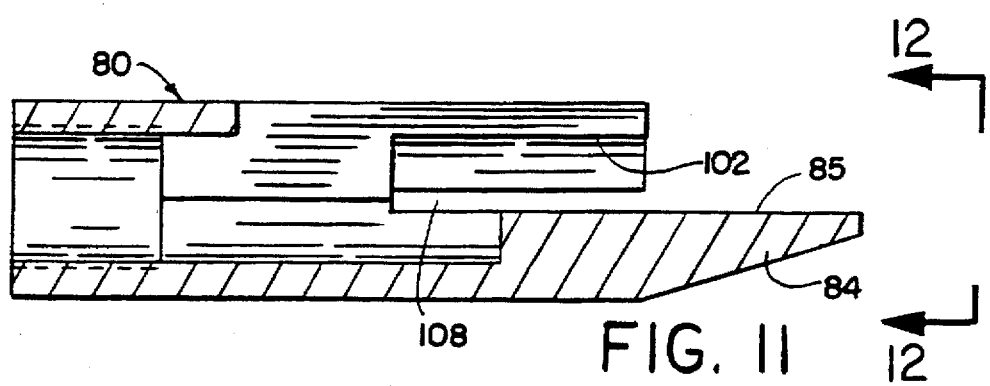
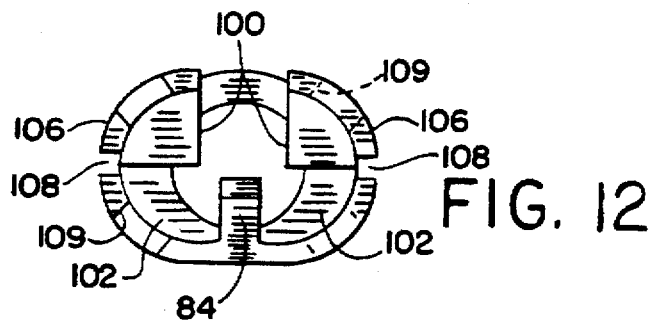
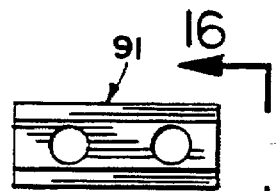
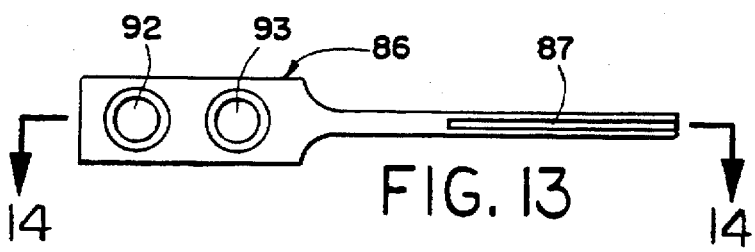
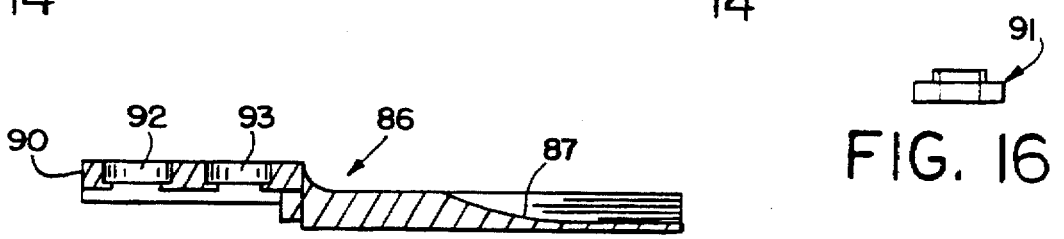
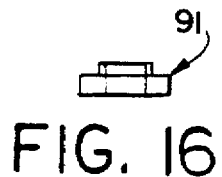

OPHTHALMIC SURGICAL INSTRUMENT AND METHOD

This application is a continuation-in-part of U.S. patent application Ser. No. 07/972,756 filed on Nov. 6, 1992, now U.S. Pat. No. 5,308,355, which application is hereby incorporated by reference in its entirety.

The invention herein described relates generally to corneal surgical procedures and instruments.

BACKGROUND

Surgical procedures to correct myopia (nearsightedness), astigmatism and hyperopia (farsightedness) have been in widespread use for at least the past 20 years. Three surgical procedures to correct these problems are radial keratotomy, astigmatic keratotomy and hexagonal keratotomy.

Radial keratotomy is used to reduce or eliminate myopia which occurs when the cornea is too steeply curved or the eyeball is too long. Blurred vision results because images focus in front of the retina. To correct for this, a series of radial incisions are made in the cornea peripherally around the central corneal zone of 3–4 mm in diameter. The incisions function to flatten the cornea and thereby move the focal point of the eye posteriorly toward the retina and ideally coincident with the retina. For optimum results, the incisions usually have to be at least 85–90% of the corneal thickness along the length thereof.

Astigmatic keratotomy corrects astigmatism caused by an irregularly shaped cornea. In an astigmatic eye, the shape of the cornea is more ovate than spherical, with the result being distorted vision. Surgical correction of the astigmatism is accomplished by placing a series of transverse incisions in opposite quadrants of the cornea. As with radial keratotomy, these incisions usually should be 85–90% of the corneal thickness.

Hexagonal keratotomy is used to correct hyperopia. Hyperopia occurs when the cornea is too flat or the eyeball is too short, whereby images focus behind the retina. To correct this problem, a "T-hexagonal" set of incisions are made in the cornea to form a six-sided geometric figure. The incisions cause the cornea inside the six-sided geometric figure to bow forward and thereby increase the curvature of the cornea and thereby move the focal point of the eye forward. This procedure has evolved since 1987 and, as currently modified by Dr. J. Charles Casebeer of Flagstaff, Ariz., has been quite successful.

At present, the above surgical procedures are for the most part done freehand by the surgeon in the following manner. The surgeon uses a pachometer, such as the Sohogage pachometer sold by Sohogage, Inc. of Cleveland, Ohio, to measure the thickness of the cornea typically 1.5 mm temporal to the visual axis or several measurements are made around the periphery of the 3–4 mm central or optical zone. The lowest reading is used to set the depth of cut of a surgical knife to be used to make the incisions. The depth of cut typically is set to 85–110% of the measured minimum thickness of the cornea depending on the surgeon's previous experience.

The success of the above surgical procedures depends in part on the ability of the surgeon to guide the knife so that it is always perpendicular to the corneal surface. Cocking of the knife to either side will result in a shallower cut. Another problem is the increase in thickness of the cornea from approximately 500 microns at the optic center to approximately 580–600 microns at the periphery of the cornea. Accordingly, the percentage depth of the cut will usually decrease moving radially outwardly along the radial incision when performing radial keratotomy.

In the past, the radial incision was made moving away from the optical zone, i.e., forward cutting (American technique), or moving towards the optical zone, i.e., reverse cutting (Russian technique). Reverse cutting was generally viewed as a more efficient and accurate procedure, but reverse cutting increased the risk of intrusion into the optical zone. Forward cutting minimized the risk of intrusion, but at the cost of a usually less square and shallower incision proximate the optical zone.

Recently, a new generation of blade was introduced. The blade, offered by Chiron Vision of Irvine, Calif., as the "DuoTrak" blade, has at opposite edges thereof a full forward cutting edge and a partial reverse cutting edge. In use, the surgeon initiates the primary incision at the optical zone and cuts downhill, i.e., radially away from the optical zone, thereby virtually eliminating potential intrusion into the central optical zone. About 1.5 mm from the limbus the direction of cut is reversed and the primary incision is enhanced, thereby overcoming the inefficiencies of forward cutting. Intrusion into the optical zone is precluded because of the configuration of the enhancement side of the blade. The result is a straight, deep, square incision with minimal risk.

Even with this enhanced double edge blade and excellent pachometry and surgeon skills, there still remains the possibility of perforation. Perforation may still arise from gross system error arising from an improper blade setting and from anatomic variation errors where the cornea is thinner at a location or locations remote from where the pachometry readings were taken. Accordingly, there continues to exist a need for surgical apparatus and methods that further reduce the threat of perforation. There also exists a need for surgical apparatus and methods that otherwise facilitate or enhance the performance of keratotomy, as by ensuring perpendicularity of the knife relative to the anterior surface of the cornea.

SUMMARY OF THE INVENTION

The present invention provides corneal surgical instruments and methods that greatly facilitate the performance of corneal surgery. An instrument according to the invention comprises a cutting blade having a cutting plane and is characterized by a pair of ultrasonic probes disposed on opposite sides of said cutting plane for measuring the thickness of the cornea. In a preferred embodiment, the probes form therebetween a window through which the cutting blade may be viewed while an incision is being made. The twin probes enable monitoring of the position and perpendicularity of a surgical knife including the cutting blade and to which the ultrasonic probes are mounted. Provision also is made for controlling the depth of the cutting blade and/or for automatic retraction of the cutting blade if the measured thickness of the cornea is too small for the depth of cut being made.

According to one preferred embodiment of the invention, the ultrasonic probes have the axes thereof equally inclined to the cutting plane and the tips thereof positioned ahead of the cutting blade. Accordingly, the probe tips are positioned in close proximity to the cutting blade and ahead of the blade to measure the thickness of the cornea ahead of the cut. Preferably, the probe tips are laterally spaced from the cutting plane by a distance less than the lateral dimension of the probe tip and form therebetween a window through which the cutting blade can be viewed.

Further in accordance with the invention, the ultrasonic probes produce an output related to the thickness of the cornea, and provision is made for processing the outputs of the ultrasonic probes to obtain an indication of the position of the cutting blade relative to the anterior surface of the cornea. In a preferred embodiment, the surgical instrument comprises a surgical microscope having a display field, and provision is made for producing in the display field a visual indication of the position of the cutting blade relative to the anterior surface of the cornea such as its perpendicularity.

The invention also provides a holder for mounting the ultrasonic probes to a surgical knife for retrofitting existing surgical knives and/or for enabling ready removal of the ultrasonic probes. Provision also is made for processing the outputs of the ultrasonic probes to obtain a measure of the thickness of the cornea and for retracting the cutting blade as a function of the measured thickness of the cornea. Retraction of the cutting blade may be automatically effected if the measured thickness is determined to be too shallow according to a preestablished criteria.

According to another aspect of the invention, there is provided a method of performing corneal surgery, comprising the steps of continuously monitoring the perpendicularity of a surgical knife during curing of the cornea, and producing in the display field of a surgical microscope a visual indication of when the surgical knife deviates from perpendicular by a predetermined mount. Preferably, the monitoring step includes the step of using a pair of ultrasonic probes to measure the thickness of the cornea at respective opposite sides of the cutting plane of the knife in close proximity to the cutting blade of the knife, and most preferably just ahead of the incision being made by the cutting blade, According to another preferred embodiment of the invention, the ultrasonic probes are used as footplates preferably in combination with a double edge blade of the above described type, i.e., a blade having at opposite edges thereof a full forward curing edge and a partial reverse cutting edge. The end faces of the probes are coplanar and contact the surface of the cornea during a surgical procedure to establish a positional relationship between the knife and the cornea. Preferably, the blade is centrally located between the tips of the two probes that are fixed to a blade housing or mount at the forward end of a surgical knife, and the probe tips are disposed laterally adjacent the cutting blade.

According to another aspect of the invention, there is provided a method of performing corneal surgery, comprising the steps of making an incision in the cornea by moving a cutting blade in a first direction, using a pair of laterally spaced apart ultrasonic transducers to repeatedly monitor the thickness of the cornea along the path of the incision while the incision is being made, outputting measured thickness information and in response thereto making any needed adjustment in the depth of the cutting blade for a reverse cut, and then making a reverse cut by moving the cutting blade along the incision in a direction opposite said first direction. The blade depth adjustment may be made by the surgeon or the depth of the cutting blade may be automatically adjusted in response to the measured thickness information prior to making the reverse cut. Preferably, the ultrasonic transducers engage the cornea to establish a positional relationship between the cutting blade and the anterior surface of the cornea.

The foregoing and other features of the invention are hereinafter fully described and particularly pointed out in the claims, the following description and the annexed drawings setting forth in detail certain illustrative embodiments of the invention, these being indicative, however, of but a few of the various ways in which the principles of the invention may be employed.

BRIEF DESCRIPTION OF THE DRAWINGS

FIG. 10 is a top plan view of a nose piece in the surgical instrument of FIG. 6.

FIG. 11 is a longitudinal sectional view of the nose piece taken along the line 11—11 of FIG. 10.

FIG. 12 is an end view of the nose piece looking form the line 12—12 of FIG. 11.

FIG. 13 is a top plan view of a blade holder in the surgical instrument of FIG. 6.

FIG. 14 is a longitudinal sectional view of the blade holder taken along the line 14—14 of FIG. 13.

FIG. 15 is a top plan view of a blade holder guide key in the surgical instrument of FIG. 6.

FIG. 16 is an end view of the blade holder guide key looking from the line 16—16 of FIG. 15.

DETAILED DESCRIPTION

The present invention will now be described in relation to two preferred embodiments respectively illustrated in FIGS. 1–5 and in FIGS. 6–22. While a particular feature of the invention may be described with respect to only one of the illustrated embodiments, such feature may be combined with one or more features of the other embodiment, as may be desired and advantageous for any given or particular application.

The FIGS. 1-5 Embodiment

Figures 1, 2:
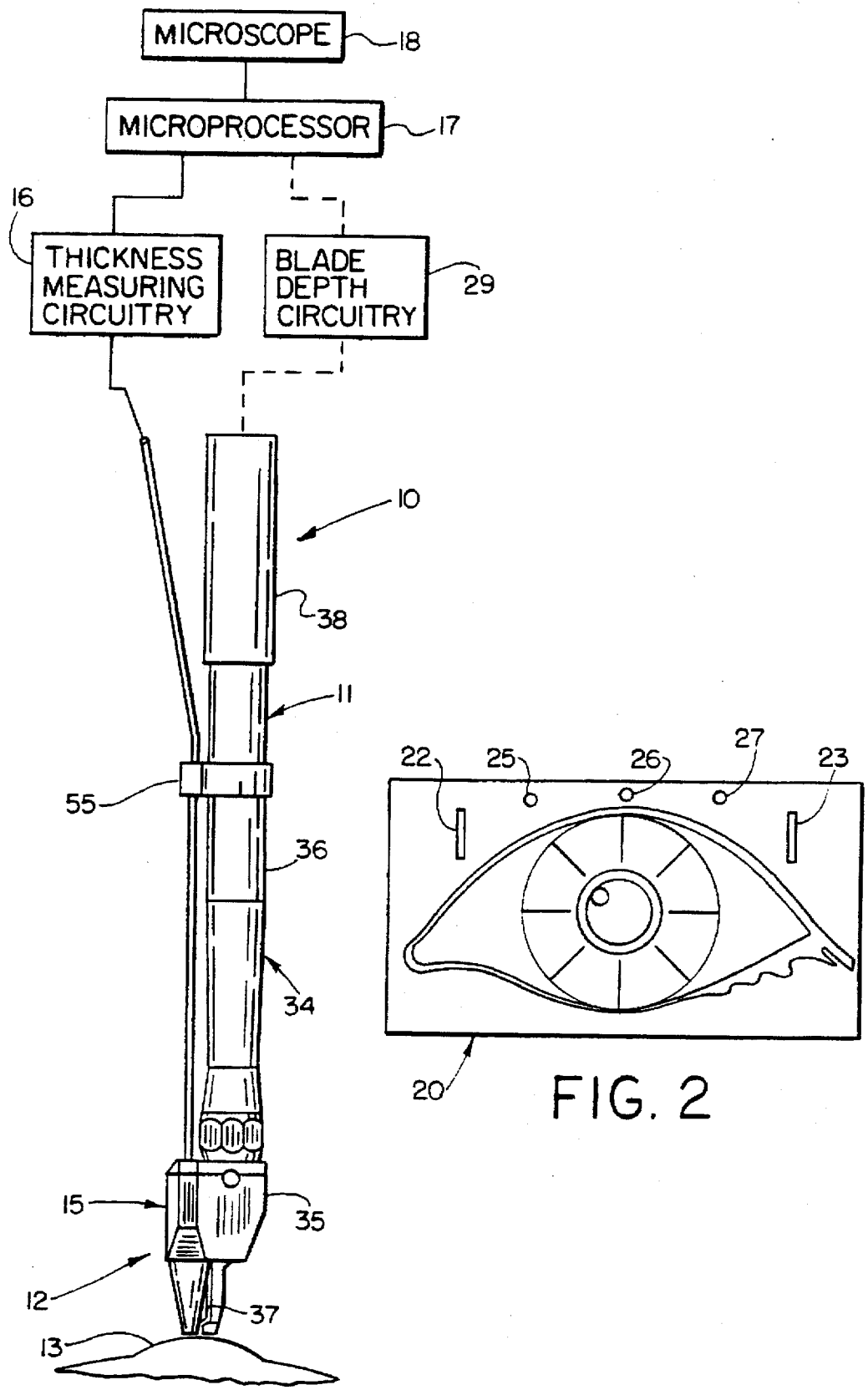
FIG. 1 is a diagrammatic illustration of a corneal surgical instrument according to the invention.
FIG. 2 is an illustration of a display of a surgical microscope.

Referring now in detail to the drawings and initially to FIG. 1, a surgical instrument according to the invention is indicated generally by reference numeral 10. The surgical instrument 10 generally comprises a surgical knife 11 and a thickness measuring device 12 for measuring the thickness of the cornea 13 in proximity to the cutting end of the knife. The thickness measuring device 12 comprises an ultrasonic probe assembly 15, thickness processing circuitry 16, and a microcomputer 17 that is interfaced to a surgical microscope 18.

In the manner described hereinafter in detail, the thickness measuring device 12 continuously monitors the thickness of the cornea just ahead of the incision being made by the knife 11. In addition, the thickness measuring device also indicates whether the knife is being held by the surgeon perpendicular to the surface of the cornea as is desired or is undesirably tilted to either side. This indication is provided within the eyepiece or display of the surgical microscope 18 used by the surgeon, as in the manner depicted in FIG. 2.

FIG. 2 represents a display field 20 as seen by a surgeon looking into the eyepiece or, more usually, the heads-up display of the surgical microscope 18. The positioning and perpendicularly of the knife are indicated by a pair of equal length, vertical lines 22 and 23 that are displayed at the upper left and right corners of the field 20. The equal length lines indicate that the knife 11 is being held perpendicularly to the surface of the cornea at the point that an incision is being made. If the surgeon is holding the knife tilted to either side, the lengths of the tilt indicator lines 22 and 23 may vary in relation to the angle of tilt with one line becoming shorter and the other longer to inform the surgeon that the knife blade is tilted so that appropriate corrective action may be taken. Additionally or alternatively, one of the tilt indicator lines may disappear if the degree of fit exceeds a prescribed amount, thereby instructing the surgeon that the knife has been tilted too far to one side and that cutting should be stopped until the knife blade is righted again as indicated by the reappearance of the indicator line that had disappeared.

The thickness measuring device 12 also functions to provide in the field of view 20 of the surgical microscope an indication that the thickness of the cornea is within an acceptable range for the depth of cut being made, is too deep or is too shallow by respectively displaying a green light 25, a red light 26 or a blue light 27. Other color lights may be used, although preferably a green light is used to indicate that the procedure may proceed while a red light is used to warn that the cutting depth is too great for the measured thickness of the cornea, at which point the surgeon should cease cutting until the blade depth setting of the knife is appropriately adjusted. The lights when displayed may be steady or blinking, as desired.

The blade depth setting may be inputted into the computer 17 for comparison with the measured thickness of the cornea either manually or by use of optional blade depth circuitry 29 (FIG. 1) connected to the knife 11. As is also further discussed below, the blade depth circuitry may optionally control the cutting depth of the knife automatically in response to the measured thickness of the cornea to maintain, for example, a constant percentage thickness cut or a cut that extends to a constant distance from the posterior surface of the cornea. However, initially, the invention will be described in relation to a surgical system which employs a conventional surgical knife, as this will show how the principles of the invention may be applied to retrofit existing manually adjustable surgical knives.

In the embodiment illustrated in FIG. 1, the surgical knife 11 is a conventional knife commonly used to perform corneal surgery. In pertinent part, the knife 11 comprises a knife body 34 including a knife blade housing 35 attached to the front end of a hollow handle 36. The blade housing 35 houses a diamond cutting blade 37 which may be adjustably extended and retracted with respect to the blade housing by a micrometer adjustment knob 38 located at the rear end of the handle 36. The blade is centrally located between two guard feet 39 that are fixed to the blade housing.

Figure 3:
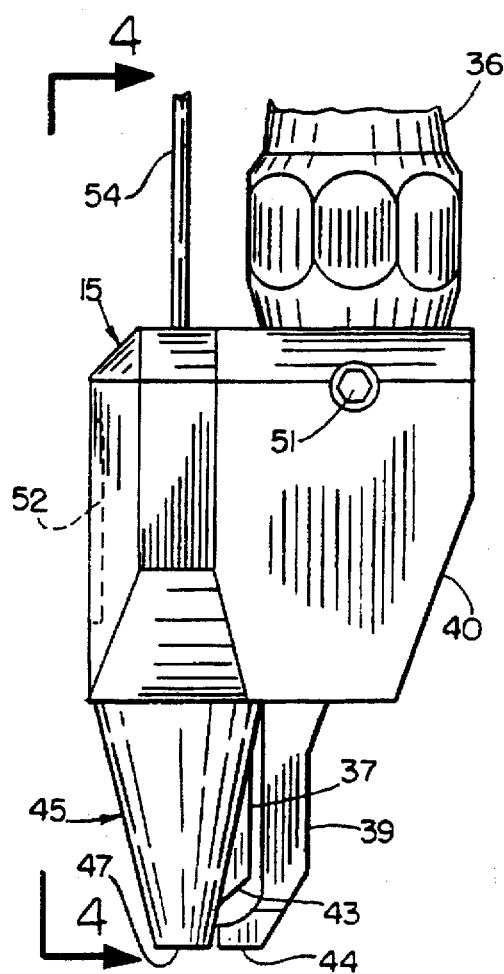
FIG. 3 is an enlarged partial side elevational view of the surgical instrument of FIG. 1 showing the cutting end of the surgical knife and ultrasonic transducer assembly thereof.

As seen in greater detail in FIG. 3, the guard feet 39, also commonly referred to as footplates, have coplanar front faces 44 intended to contact the surface of the cornea during a surgical procedure to establish a positional relationship between the knife and the cornea. Adjustment movement of the cutting blade 37 is in a direction perpendicular to the plane of the front faces 44, and the amount of extension of the cutting blade beyond the plane of the front faces 44 thereby determines the depth of penetration of the blade into the cornea. As is customary, the knife is calibrated using precision equipment so that the precise amount of extension can be selected by the surgeon by using a micrometer gauge associated with the micrometer adjustment knob 38.

The cutting end of the blade 37 has a well known configuration. The blade is a thin planar member having parallel flat sides terminating at a cutting edge 43 which is usually inclined relative to the longitudinal axis of the blade. In presently used blades, the angle formed between the cutting edge and the longitudinal axis of the blade generally is in the range of 10 to 45 degrees, although squared edge blades also are used for performing straight "T" incisions during astigmatic keratotomy.

Figure 4:
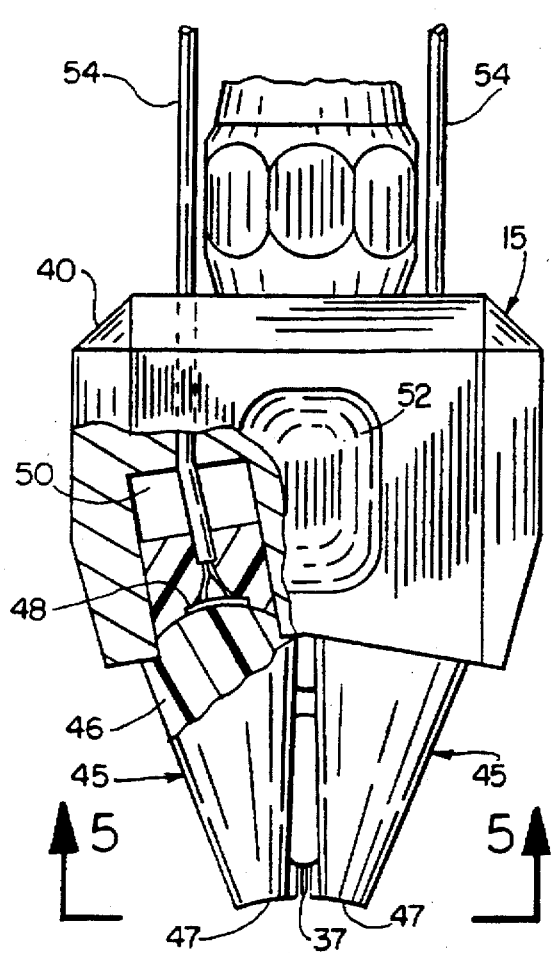
FIG. 4 is a partial top plan view, partly broken away in section, of the surgical instrument taken from the line 4—4 of FIG. 3.
Figure 5:
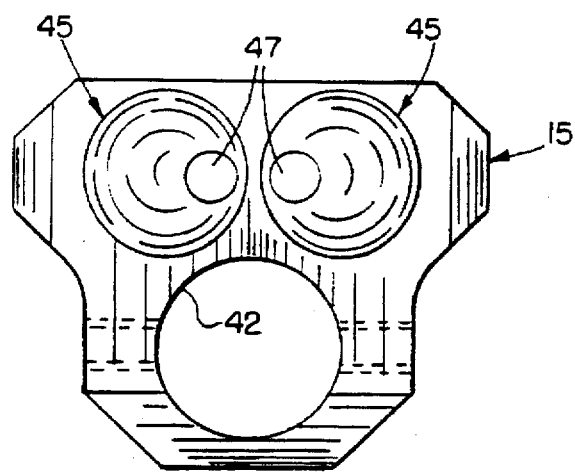
FIG. 5 is an end view of the ultrasonic transducer assembly taken from the line 5—5 of FIG. 4.

With reference to FIGS. 3-5, the ultrasonic probe or transducer assembly 15 comprises a holder 40 secured to the blade housing 35 of the knife 11. In the illustrated embodiment, the holder is designed to be separable from the knife. To this end, the holder has a rearwardly opening socket 42 configured to receive with a close fit the rear barrel end of the blade housing. Since the illustrated blade housing has a cylindrical rear barrel end, the socket 42 is likewise cylindrical so that the holder may be telescopically slipped onto the blade housing. The holder is held securely, but removably, in place by a pair of diametrically opposed set screws 43 or other suitable means.

On its top surface, the holder has a shallow finger recess 44 or the equivalent as an aid in providing positive engagement with the finger of a surgeon. Many surgeons use a two-hand procedure for manipulating the knife. The handle of the knife is held by one hand while one of the fingers of the other hand, usually the index finger, is pressed against the top of the knife housing to steady and guide the cutting blade while an incision is being made. The present holder and finger recess enable a positive engagement between the surgeon's finger and the cutting end of the knife. The bottom of the finger recess may be provided with laterally extending ribs, knurling or the like.

The holder 40 functions as a mount for a pair of ultrasonic thickness measuring probes 45 that individually may be of conventional type. Accordingly, and as best seen at the left in FIG. 3, each ultrasonic probe 45 includes a conical contact head 46, also referred to as a delay line, having a circular tip 47 for contacting the surface of the cornea. At its distal end, the contact head 46 has a dome-shaped rear end surface to which an ultrasonic transducer element, i.e., a piezoelectric crystal 48, is coupled and secured in place by an epoxy backing 49. The rear end of the ultrasonic probe 45 is fixed in a cylindrical socket 50 in the holder.

The piezoelectric crystal 48 of each ultrasonic probe 45 is operatively connected to the wire leads of an electrical cable 54 which extends out through the back end of the holder for connection to the thickness measuring circuitry 16 (FIG. 1). Preferably, the cable 54 is run along the length of the knife body and held in place by one or more retention bands 55.

As is well known, the circuitry 16 may be operated to pulse the piezoelectric crystal in order to generate a 20 MHz beam. The beam is directed along the axis of the contact head which focusses the beam at a point located forwardly of the probe tip 47 so that the focal point will lie interiorly of the cornea when the probe tip contacts the outer surface of the cornea. The 20 MHz pulse that is generated will result in a first echo corresponding to the anterior corneal surface and a second echo corresponding to the posterior corneal surface. The difference in time of these two echoes received back at the transducer 48 is a measure of the corneal thickness, as the time between the reflected echoes can be converted in known manner to a distance which will be the thickness of the cornea along the probe axis at the point the probe contacts the cornea. By repeatedly pulsing the transducer and detecting the echoes, the thickness of the cornea may be continuously monitored and reported by the depth measuring circuitry to the computer 18, respectively. Individually, the ultrasonic probes and associated ultrasonic depth measuring circuitry have been used in prior art devices including, in particular, Sonogage pachometers sold by Sonogage, Inc. of Cleveland, Ohio.

Although the ultrasonic probes 45 individually fall within the prior art as just indicated, two such probes are uniquely combined and related to a surgical knife in a manner that overcomes problems associated with prior art corneal surgical equipment and procedures. As seen in FIGS. 3–5, the two probes 45 are located at respective opposite sides of the cutting plane of the cutting blade with the axes thereof preferably residing in a common plane that is parallel to the longitudinal axis of the cutting blade and perpendicular to the cutting plane of the cutting blade or, more generally, perpendicular to the cutting direction of the cutting blade. In general, the cutting plane of the cutting blade is the plane defined by the longitudinal axis of the curing blade and the direction in which the blade is intended to cut (the cutting direction in FIG. 3 is right to left). In the case of a flat planar cutting blade as shown, the cutting plane of the cutting blade coincides with the major planar extent of the cutting blade. What is desired is that the ultrasonic probes and, more particularly, the tips thereof are disposed on opposite sides of the movement path of the blade and equally laterally spaced from such movement path.

In addition, the probes preferably are oriented to bring the tips thereof into close proximity to the movement path of the cutting blade. To this end, the probes are inclined in the common plane thereof such that their axes are inclined to the cutting plane of the cutting blade at the same included angle. In the illustrated embodiment, the axis of each probe forms with the cutting plane of the cutting blade an angle of about 10 degrees. Moreover, the axes of the two probes preferably intersect at a point located about 7.50 mm in front of their probe tips, such dimension being about the average radius of curvature of the cornea. Accordingly, the probe axes will extend perpendicularly to the anterior surface of the cornea when the longitudinal axis of the knife is perpendicular to such surface. The longitudinal axis of the knife bisects the angle formed between the axes of the probes.

In addition, the tips of the probes are located ahead of the feet 39 and more particularly the cutting blade. As a result, the probes will operate to measure the thickness of the cornea ahead of the cutting blade rather than coincidentally with the cut. This affords better protection in those situations where the thickness of the cornea varies rapidly and unexpectedly as the cut is being made. In an alternative embodiment, such as the hereinafter described embodiment of FIGS. 6–22, the probes may function as the feet whereby the feet may be eliminated. In this alternative arrangement, the probe tips preferably are disposed laterally adjacent the cutting blade rather than spaced ahead of the cutting blade.

In the embodiment illustrated in FIGS. 1–5, the tips of the probes are spaced ahead of the cutting edge of the curing blade by about 2 mm. Each probe tip has a diameter of about 1.5 mm and the tips are laterally spaced apart to provide a window having a width of about 0.7 mm through which the cutting blade can be viewed by the surgeon when making an incision. Of course, such window will appear relatively large when viewed on the heads-up display of the surgical microscope. If desired, the width of the window may be increased by more sharply tapering the adjacent inner sides of the conical contact heads.

As seen in FIGS. 3 and 4, the tips of the probes are tangential to an arc common with the front faces 44 of the feet 39. That is, the probe tips will contact the cornea when the feet are brought into contact with the cornea, provided the knife is oriented perpendicularly to the anterior surface of the cornea. If the knife is tilted to either side, this will be detected in the below described manner. If the knife is tilted in a direction opposite the cut direction, this will lift the probes out of contact with the cornea and this will be indicated by the spurious readings received by the computer. Regarding tilting of the knife in the direction of cutting movement, this normally will occur infrequently and the only consequence is a shallow cut. Also, such tilting will give a false reading that the thickness is greater than it actually is until the probes are sufficiently tilted that they will provide spurious measurements to the computer.

In use, the two probes 45 are used to make corneal thickness measurements. The measurements may be based on an averaging of multiple, such as 500, sets of echoes that are sampled from each transducer. The microprocessor takes the thickness measurements made by the two transducers at the same or substantially the same time and compares them. If the difference between the two thickness measurements is greater than a prescribed amount, such as 5 microns, then a signal is sent to the display 20 to indicate an unacceptable degree of knife tilt, such as by blanking out the vertical lines 22 and 23, causing the tilt indicator lines to blink, or other indicating scheme that may be desired. If the difference is less than the prescribed amount, the tilt indicator lines may remain uniform.

The two thickness measurements also are averaged and compared to the blade setting that has been inputted into the computer or automatically sensed by the blade depth circuitry 29 (FIG. 1). If the average measurement is within a prescribed amount, for example 5 microns, of the blade setting value, the green light on the display 20 is turned on to inform the surgeon that the cornea thickness is within an acceptable range, such as plus or minus 5 microns of the set amount. If the blade setting exceeds the average measured thickness by more than the prescribed amount, the red light is blinked to warn of too deep of cut. If the average measured thickness exceeds the blade setting by more than the prescribed amount, the blue light is blinked to warn that the cut is too shallow.

Preferably the foregoing measurement and comparison operations are repeated continuously at a suitable frequency of say 10 times a second.

As above indicated, the blade depth circuitry 29 (FIG. 1) may have provision for automatically controlling the cutting depth of the knife in response to the measured thickness of the cornea to maintain, for example, a constant percentage thickness cut or a cut that extends to a constant distance from the interior surface of the cornea. In this modified arrangement, the adjustment knob 38 (FIG. 1) may be replaced by a suitable blade drive mechanism including, for example, a stepping motor and appropriate circuitry for operating the stepping motor and providing positive feedback of the cutting depth of the blade. Then, the position of the blade may be controlled by the computer in programmed response to cornea thickness measurements made by the ultrasonic probes. If the measured thickness is less than the blade depth setting by a prescribed amount, the computer not only can provide the above described visual warning to the surgeon but it can also automatically retract the cutting blade. In a more automated system, the microprocessor may be programmed to automatically vary the cutting depth of the cutting blade in response to the measured thickness of the cornea to maintain, for example, a constant percentage thickness cut or a cut that extends to a constant distance from the posterior surface of the cornea.

As above described and shown in FIGS. 3-5, the probe assembly is a separate structure that can be assembled onto and removed from the knife. As above indicated, this lends itself to retrofitting existing surgical knives. Additionally, the probe assembly may be removed for sterilization apart from the knife or for disposal and replacement with another probe assembly. Notwithstanding these advantages, the invention also contemplates an integrated knife and probe assembly wherein the probes are integrally assembled into the knife body independently of any removable holder. This will provide for a more compact structure and will allow the probe wiring to be run through the knife body.

Another advantage afforded by the invention is a self-checking feature that arises from the use of two probes for measuring the thickness of the cornea. If one probe goes bad and starts giving incorrect thickness readings, this will become immediately evident by comparison with the readings provided by the still properly functioning probe. By virtue of the foregoing logic, the surgeon will be informed that he has lost perpendicularity. Upon realizing that in fact he has not lost perpendicularity, the surgeon will know that there is a malfunction in the system.

The FIGS. 6-22 Embodiment

Figure 7:
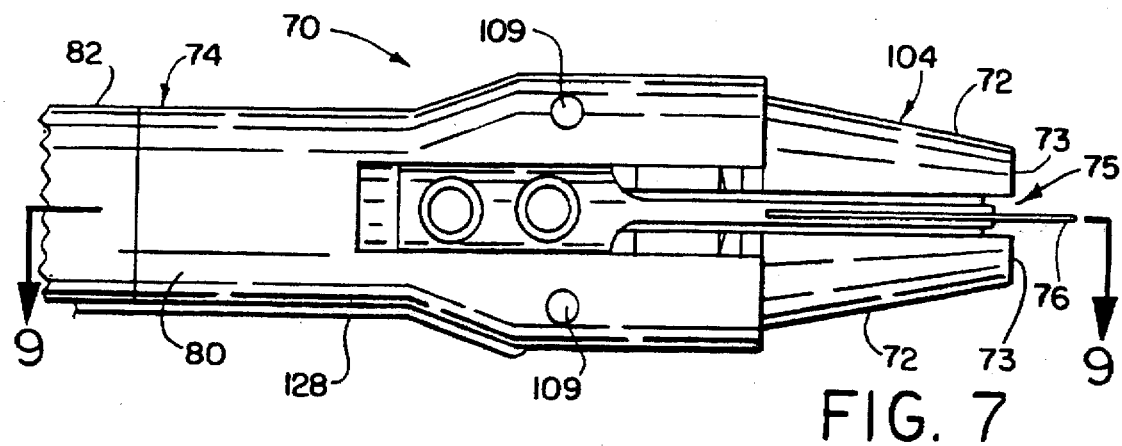
FIG. 7 is a top plan view of the surgical instrument of FIG. 6 looking from the line 7—7 thereof.
Figure 6:
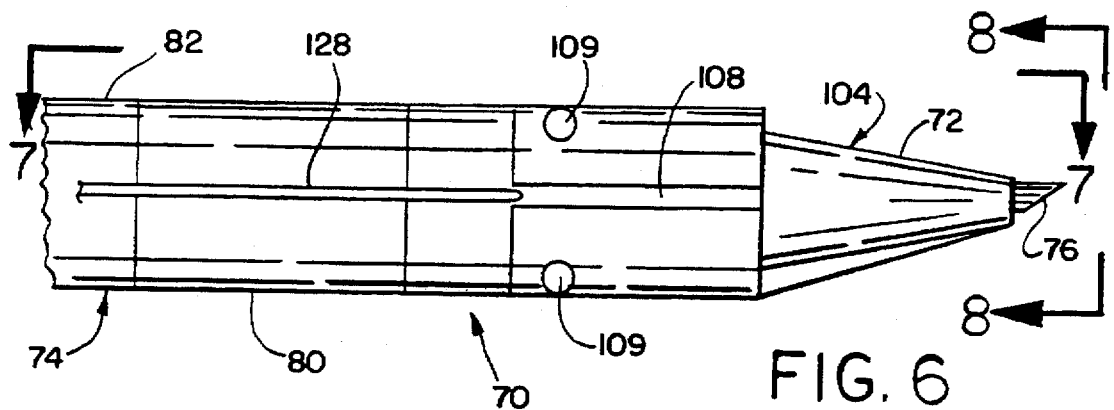
FIG. 6 is a side elevational view of the nose end of another embodiment of surgical instrument according to the invention.
Figure 8:
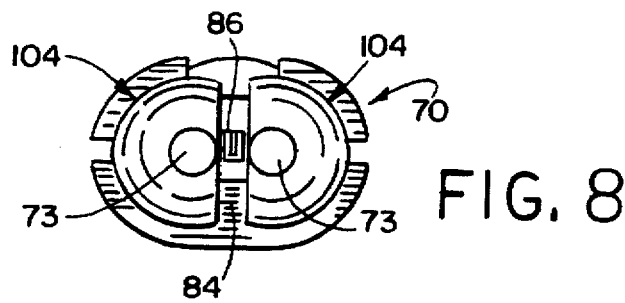
FIG. 8 is an end view of the surgical instrument of FIG. 6 looking from the line 8—8 thereof.
Figure 9:
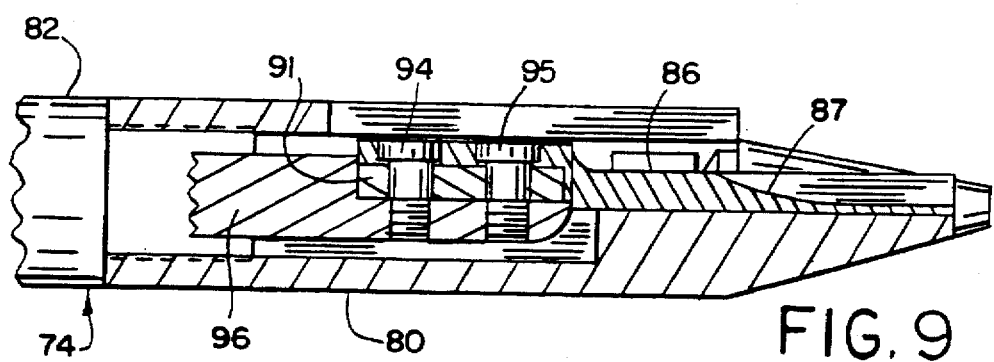
FIG. 9 is a longitudinal sectional view of the surgical instrument of FIG. 6 taken along the line 9—9 of FIG. 7.

Referring now to FIGS. 7-9, another preferred embodiment of a surgical instrument according to the invention is illustrated at 70. The instrument 70 generally is in the form of a surgical knife although only the forward portion thereof is illustrated. The remainder of the knife may be of conventional design or as above described. In this embodiment, the probes 72 additionally perform the function of the aforedescribed guard feet, i.e., the front faces 73 of the probes contact the surface of the cornea during a surgical procedure to establish a positional relationship between the knife body 74 and the cornea, and thereby determine the cutting depth of the cutting blade. At the same time, the probes may be used to perform pachometry. As in the abovedescribed embodiment of FIGS. 1-5, the tips of the probes are laterally spaced apart to form therebetween a window 75 through which the cutting blade 76 of the knife 70 may be viewed while an incision is being made.

In the embodiment of FIGS. 6-9, a blade housing or nose piece 80 is formed as a discrete member having at its rear end a threaded bore for threaded securement to the forward end of a hollow knife handle 82. As will be appreciated by those skilled in the art, the nose piece may be mounted to the handle by other suitable means or it may be formed integrally with the handle, as may be desired.

As seen in FIGS. 10-12, the nose piece 80 has a longitudinally extending forward projection 84 that is laterally centered with respect to the longitudinal axis of the nose piece and consequently the longitudinal axis of the knife. The forward projection 84 has a sloped underside and a top support or platform surface 85. The top platform surface supports a cutting blade holder 86 for longitudinal sliding movement thereon as shown in FIG. 9. The blade holder 86, which is further shown in FIGS. 13 and 14, has at its forward end a narrow longitudinally extending slot 87 for holding a cutting blade. The cutting blade shown in FIGS. 6 and 7 at 76, may be secured by conventional means in the slot, as by using a bonding agent or other suitable means.

At its rearward end the cutting blade holder 86 is provided with a reduced thickness tongue 90 that is recessed at its underside for receiving a blade holder guide key 91 (FIGS. 15 and 16). The tongue is provided with a pair of longitudinally spaced apart holes 92 and 93 (FIGS. 13 and 14) through which respective fasteners such as screws 94 and 95 extend for securing the tongue to the forward end of a drive shaft 96 of the knife as shown in FIG. 9. The drive shaft provides the link between the blade holder 86 and the knife's blade adjustment mechanism, which mechanism may be manually or automatically adjusted as abovedescribed.

As shown in FIG. 9, the blade holder guide key 91 is sandwiched between the blade holder tongue 90 and the drive shaft 96. The guide key is guided between a pair of opposed guide surfaces 100 (FIG. 12) formed in the nose piece 80 for longitudinal movement parallel to the longitudinal axis of the nose piece. The coaction between the guide key 91 and the guide surfaces 100 prevents lateral shifting movement of the blade holder 86 relative to the nose piece.

The nose piece 80 also includes probe mounting structure such as, for example, a pair of receptacles or sockets 102 (FIG. 12) for receiving an ultrasonic probe assembly or assemblies 104 including the probes 72. The inner side of each socket is formed by the forward projection 84 while the outer side of each socket is formed by an arcuate wall 106 as shown in FIG. 12. The arcuate wall 106 has a central longitudinal slot 108 and one or more apertures 109 formed therein for reasons discussed hereinafter.

Each ultrasonic probe assembly 104 includes a probe holder 112 (FIGS. 20-22) configured to be inserted with a close fit in a respective one of the sockets 102 in the nose piece 80. As is preferred, the probe holder 112 is releasably attached to the nose piece. In the illustrated embodiment the probe holder is provided with one or two latches 114 which cooperate with the apertures 109 in the nose piece to hold the probe holder in the socket 102 while permitting relatively easy removal of the holder when the ultrasonic probe assembly is to be separated from the knife body. Each illustrated latch includes one or more transversely detectable arms 116 (two being preferred as shown) that extend rearwardly from a holder body 118. The arm 116 has at its distal end a radially outwardly protruding catch 119 for engaging in a respective apertures 109 in the nose piece. Each catch is provided with a ramp surface 120 that engages the socket wall 106 to cammingly deflect the arm 116 radially inwardly for passage of the catch along the side wall. When the catch becomes aligned with the corresponding aperture 109 after full insertion of the probe holder into the socket, the catch will spring radially outwardly and engage within the aperture to prevent withdrawal of the probe holder from the socket. To remove the probe assembly, the catches may be urged radially inwardly to clear the apertures to permit axial withdrawal of the probe holder from the socket. The catches may be conveniently disengaged by using, for example, a suitable tool having a pair of detents positioned such that they can be aligned with the apertures 109 associated with either one of the probe holders and then moved into the apertures to displace the catches sufficiently to release them with respect to the nose piece.

The probe holders 112 function as mounts for the ultrasonic thickness measuring probes 72 that may be of conventional type and preferably the above described type. Although two discrete probe holders are shown in the illustrated embodiment, the ultrasonic probes may be mounted in a single probe holder that may be conveniently attached or removed from the nose piece of the knife as a single unit. In either case, it may be desirable to provide suitable means for longitudinally adjusting the position of the probe assembly or assemblies relative to the knife body to bring the tips into a desired zero position relative to the permitted range of movement of the cutting blade.

Figure 17:
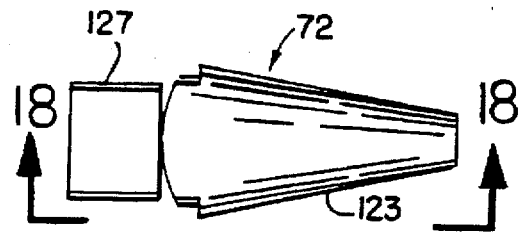
FIG. 17 is a side elevational view of an ultrasonic transducer in the instrument of FIG. 6.
Figure 18:
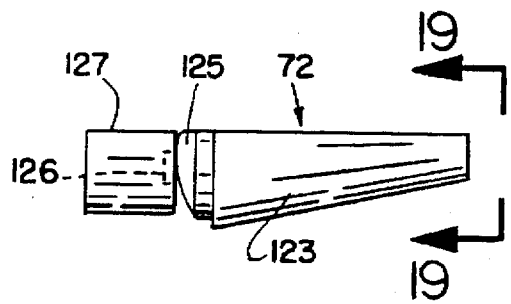
FIG. 18 is a view of the ultrasonic transducer looking from the line 18—18 of FIG. 17.
Figure 19:
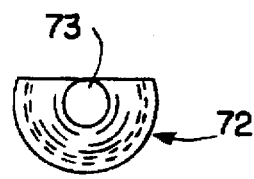
FIG. 19 is and end view of the ultrasonic transducer looking from the line 19—19 of FIG. 18.
Figure 20:
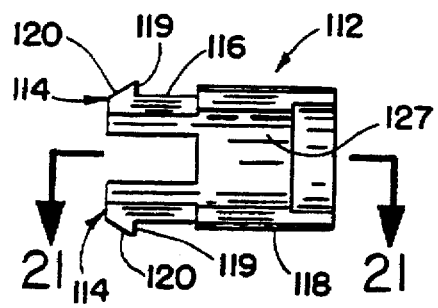
FIG. 20 is an elevational view of a transducer holder in the surgical instrument of FIG. 6.

As best seen at the left in FIGS. 17–19, each ultrasonic probe 72 includes a conical contact head 123, also referred to as a delay line, having a circular tip 73 for contacting the surface of the cornea. At its distal end, the contact head has a dome-shaped rear end surface 125 to which an ultrasonic transducer element 126, e.g., a piezoelectric crystal or polymer (polyvinylideneflouride) film, is coupled and secured in place by an epoxy backing in a C-shape case 127. The rear end of the ultrasonic probe is fixed by suitable means, such as by epoxy, in the interior region or socket 127 of the holder body 118 which can be seen in FIG. 22 to have a generally C-shape.

The piezoelectric crystal 126 of each ultrasonic probe 72 is operatively connected to the wire leads of an electrical cable 128 (FIGS. 6 and 7) which extends out through the back end of the holder for connection to thickness measuring circuitry, such as the thickness measuring circuitry 16 described in relation to the embodiment of FIGS. 1–5. When the probe assembly is being inserted into the socket in the knife body forward end portion, the cable 128 may be conveniently passed through the slot 108 in side wall of the socket. From the slot 108, the cable may be run along the length of the knife body and held in place by one or more retention bands as above described in relation to the embodiment of FIGS. 1–5. In another exemplary arrangement, the connecting cable may be terminated at an electrical connector in the probe assembly which mates with an electrical connector in the nose piece when the probe assembly or assemblies are assembled to the nose piece, thereby to facilitate ready attachment and removal of the probe assembly or assemblies. The electrical leads running from the electrical connector in the nose piece may be run through an interior passage through the knife body.

The cable 128 connects the probes to circuitry such as that above described in relation to the FIGS. 1–5 embodiment. The measuring circuitry may be operated to pulse the piezoelectric crystal in order to generate a 20–100 MHz beam. The beam is directed along the axis of the contact head which focusses the beam at a point located forwardly of the probe tip so that the focal point will lie interiorly of the cornea when the probe tip contacts the outer surface of the cornea. The 20–100 MHz pulse that is generated will result in a first echo corresponding to the anterior corneal surface and a second echo corresponding to the posterior corneal surface. The difference in time of these two echoes received back at the transducer 72 is a measure of the corneal thickness, as the time between the reflected echoes can be converted in known manner to a distance which will be the thickness of the cornea along the probe axis at the point the probe contacts the cornea. By repeatedly pulsing the transducer and detecting the echoes, the thickness of the cornea may be continuously monitored and reported by the depth measuring circuitry to the therewith associated computer.

The ultrasonic probes may have the axes thereof equally inclined to the cutting plane such that the axes thereof extend perpendicular to the anterior surface of the cornea when the plane of the cutting blade is perpendicular to the anterior surface of the cornea. However, in the illustrated embodiment, the tips of the probes are planar surfaces that reside in a common plane perpendicular to the plane of the cutting blade. Also, the tips of the probes are positioned laterally adjacent and in close proximity to the cutting blade. Preferably, the probe tips are laterally spaced from the cutting plane by a distance less than the lateral dimension of the probe tip and form therebetween the aforesaid window through which the cutting blade can be viewed.

Figure 23:
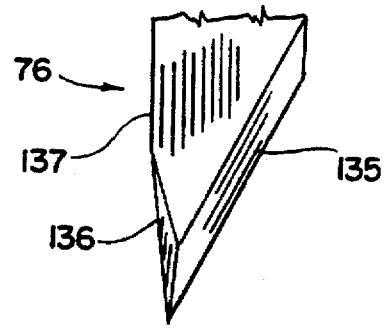
FIG. 23 is an enlarged partial elevational view of a preferred cutting blade.
Figure 21:
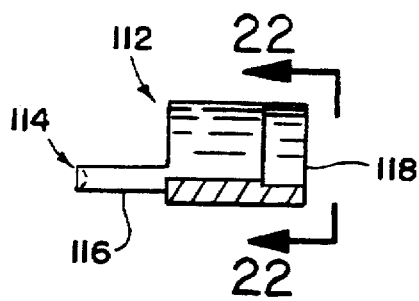
FIG. 21 is a longitudinal sectional view of the holder taken along the line 21—21 of FIG. 20.
Figure 22:
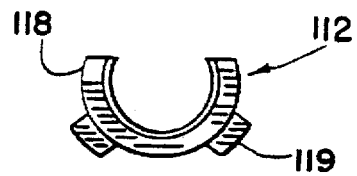
FIG. 22 is an end view of the nose piece looking from the line 22—22 of FIG. 21.

As above indicated, the surgical instrument 70 is particularly suited for use with a double edge blade of the type sold by Chiron Vision as the "DuoTrak" blade. As shown in FIG. 23, this blade 76 has at opposite edges thereof a full forward cutting edge 135 and a partial reverse cutting edge 136. The reverse cutting edge 136 is parallel to the longitudinal extent or axis of the blade whereas the forward cutting edge 135 is inclined relative to the blade axis and meets the reverse cutting edge at a pointed tip. The reverse cutting edge has a length less than the forward cutting edge whereby it is capable of cutting only at the distal end of the blade, for example, the distal 200 microns of the blade, which is less than half the available cutting length of the forward cutting edge. The partial reverse cutting edge terminates at a relatively blunt upper reverse edge portion 137 that presents a generally flat face that is generally parallel to the blade axis.

The surgical instrument (knife) 70 may be used in known manner to perform kerortorefractive surgery. However, the surgical procedure is enhanced by reason of the unique characteristics of the instrument 70. In customary manner, the patient lies on an operating table and looks up. The surgeon views the patient's eye through the heads-up display of an operating microscope, asking the patient to fixate on a light filament in the microscope. The surgeon then customarily marks the cornea with an optical zone marker and a radial cut marker. The purpose of the optical zone marker is to designate the inner limit of the radial cut. Invasion of the optical zone is to be avoided. However, it is desirable to have a square cut at the optical zone mark.

With the cutting blade retracted relative to the tips of the probes, the probes may be used to measure the thickness of the cornea to obtain a thickness reading or reading from which the desired depth of cut can be determined. Alternatively, a separate pachometer may be used to make the initial thickness measurements. A measurement may be made, for example, 1.5 mm temporal to the visual axis or several measurements may be made around the periphery of the optical zone. The lowest reading typically will be used to set the depth of cut of the cutting blade. The depth of cut typically will be set 85–110% of the measured minimum thickness of the cornea.

According to established prior art procedures, each radial incision is made by starting at the central optical zone and moving the blade forwardly (forward cutting) toward the limbus and then returning in the same incision (reverse cutting) to achieve consistent depth and to square off the incision at the central optical zone. Upon reaching the optical zone the blade is inhibited from advancing into the optical zone by the uncut tissue superior to the 200 micron cutting surface on the reverse edge of the blade. That is, the blunt upper reverse edge portion 137 is obstructed by the uncut tissue.

In accordance with the present invention, the ultrasonic probes, which function as footplates, also are used to perform pachometry along the incision path and preferably while the forward incision is being made. If the thickness of the cornea is found to be smaller than the blade depth setting, then a warning may be issued to the surgeon or the blade setting may be adjusted automatically before the reverse cut is made. As will be appreciated, the forward cut is usually shallow relative to the reverse cut because of the nature of the modified double edge blade. Accordingly, there is minimal chance of perforation happening during the forward cut. Only during the reverse cut is there increase risk of perforation, but this is avoided by the present invention as aforedescribed. That is, the thickness measurements made during the forward cut provide for detection of any relatively thin regions of the cornea along the path of the cut and provision is made for warning the surgeon to adjust the blade depth shallower for the reverse cut or for automatically adjusting the blade. Of course, these functions are performed by the ultrasonic probes through interaction with a computing device such as thickness processing circuitry interfaced with a microcomputer as aforedescribed in relation to the FIGS. 1-5 embodiment.

If desired, a visual warning or indication may be displayed in the view window of a surgical microscope to advise the surgeon of the need to change the blade depth or that the blade depth is being adjusted automatically. As is preferred, the measured thickness of the cornea (which may be an average of the thicknesses measured by the two probes) may be displayed in real time in the view window of the microscope or otherwise while the surgeon is making the incision during the forward and reverse cuts. Also, audio warnings and/or cues may be provided using well known techniques.

In addition to continuously monitoring the thickness of the cornea as the incision is being made, the thickness measuring device also indicates whether the knife is being held by the surgeon perpendicular to the surface of the cornea as is desired or is undesirably tilted to either side. This indication may be provided within the eyepiece or display of the surgical microscope used by the surgeon, as described above in connection with the FIGS. 1-5 embodiment. Likewise, the ultrasonic probes and associated thickness measuring components may function to provide in the field of view of the surgical microscope an indication that the thickness of the cornea is within an acceptable range for the depth of cut being made, is too deep or is too shallow by respectively displaying a green light, a red light or a blue light, as above described in relation to the FIGS. 1-5 embodiment.

As above described and shown, the probe assembly is a separate structure that can be assembled onto and removed from the knife. Accordingly, the probe assembly may be removed for sterilization apart from the knife or for disposal and replacement with another probe assembly. Notwithstanding, the invention also contemplates an integrated knife and probe assembly wherein the probes are integrally assembled into the knife body independently of any removable holder.

As above described in connection with the embodiment of FIGS. 1-5, a self-checking feature is provided by the use of two probes for measuring the thickness of the cornea. If one probe goes bad and starts giving incorrect thickness readings, this will become immediately evident by comparison with the readings provided by the still properly functioning probe. By virtue of the foregoing logic, the surgeon will be informed that he has lost perpendicularity. Upon realizing that in fact he has not lost perpendicularity, the surgeon will know that there is a malfunction in the system.

Although the invention has been shown and described with respect to certain preferred embodiments, equivalent alterations and modifications will no doubt occur to others skilled in the art upon the reading and understanding of this specification. The present invention includes all such equivalent alterations and modifications, and is limited only by the scope of the following claims.

What is claimed is:

1. A method of performing corneal surgery, comprising the steps of making an incision in the cornea by moving a cutting blade in a first direction, using a pair of laterally spaced apart ultrasonic transducers to repeatedly monitor the thickness of the cornea along a path of the incision while the incision is being made, outputting measured thickness information and in response thereto making any needed adjustment in the depth of the cutting blade for a reverse cut, and then making a reverse cut by moving the cutting blade along the incision in a direction opposite said first direction.

2. A method as set forth in claim 1, including the step of monitoring the perpendicularity of a plane of the cutting blade during cutting of the cornea, and producing in a display field of a surgical microscope a visual indication of when the cutting blade deviates from perpendicular by a predetermined amount.

3. A method as set forth in claim 1, wherein the depth of the cutting blade is automatically adjusted in response to the measured thickness information prior to making the reverse cut.

4. A method as set forth in claim 1, wherein the ultrasonic transducers engage the cornea to establish a positional relationship between the cutting blade and the anterior surface of the cornea while the incision is being made.

5. A method as set forth in claim 1, further comprising the step of:
    releasably securing the ultrasonic transducers to a surgical knife that includes the cutting blade for facilitating removal of the ultrasonic transducers from the surgical knife as part of a repair or sterilization step.

6. A method as set forth in claim 5, wherein the releasably securing step is accomplished with at least one releasable latch.

7. A method as set forth in claim 1, wherein the step of using the ultrasonic transducers includes monitoring the thickness of the cornea just ahead of the cutting blade along the path of the incision.

8. A method of performing corneal surgery using a surgical instrument having a knife body and a cutting blade, the method comprising the steps of:
    cutting the cornea in a first direction by moving the cutting blade from an edge of an optical zone away from the optical zone to form an incision, the cutting blade having at opposite edges thereof a full forward cutting edge and a partial reverse cutting edge with the full forward cutting edge facing the first direction;
    continuously monitoring the thickness of the cornea along the path of the incision while the incision is being made using a pair of laterally spaced apart ultrasonic transducers releasably secured to the knife body;

outputting measured thickness information and in response thereto making any needed adjustment in the depth of the cutting blade for a reverse cut; and cutting the cornea by moving the cutting blade along the incision in a direction opposite said first direction, the partial reverse cutting edge inhibiting the cutting blade from entering the optical zone.

9. A method as set forth in claim 8, including the step of monitoring the perpendicularity of a plane of the cutting blade, and producing in a display field of a surgical microscope a visual indication of when the cutting blade deviates from perpendicular by a predetermined amount.

10. A method as set forth in claim 8, wherein during the cutting steps the depth of the incision made by the cutting blade is automatically adjusted in response to the measured thickness information prior to making the reverse cut.

11. A method as set forth in claim 8, wherein during the monitoring step the ultrasonic transducers engage the cornea to establish a positional relationship between the cutting blade and the anterior surface of the cornea while the incision is being made.

12. A method as set forth in claim 8, further comprising the step of:

releasably securing the ultrasonic transducers to the knife body for facilitating removal of the ultrasonic transducers as part of a repair or sterilization step.

13. A method as set forth in claim 12, wherein the releasably securing step is accomplished with at least one releasable latch.

14. A method as set forth in claim 8, wherein the monitoring step includes monitoring the thickness of the cornea ahead of the cutting blade in the first direction.

* * * * *